United States Patent [19]

Marangoni

[11] Patent Number: 4,535,783
[45] Date of Patent: Aug. 20, 1985

[54] PERSONAL ELECTROCARDIOLOGY RECORDER

[75] Inventor: Daniele Marangoni, Milan, Italy

[73] Assignee: Kontron Holding A.G., Zurich, Switzerland

[21] Appl. No.: 518,859

[22] Filed: Aug. 1, 1983

[30] Foreign Application Priority Data

Aug. 5, 1982 [CH] Switzerland ............... 4717/82

[51] Int. Cl.³ .................................. A61B 5/04
[52] U.S. Cl. ............................ 128/711; 128/696; 128/639
[58] Field of Search ............ 128/637, 639, 641, 696, 128/701, 707, 710–711

[56] References Cited

U.S. PATENT DOCUMENTS

| | | | |
|---|---|---|---|
| 2,660,175 | 11/1953 | Thrasher et al. | 128/643 |
| 3,229,687 | 1/1966 | Holter et al. | 128/711 |
| 3,505,993 | 4/1970 | Lewes et al. | 128/643 |
| 3,792,700 | 2/1974 | Sarnoff et al. | 128/639 |
| 3,848,582 | 11/1974 | Milani et al. | 128/639 |
| 3,858,576 | 1/1975 | Dehnert et al. | |
| 3,913,567 | 10/1975 | Streckmann | 128/711 |
| 3,934,267 | 1/1976 | Kosaka et al. | 128/711 |
| 4,004,577 | 1/1977 | Sarnoff | 128/639 |
| 4,015,596 | 4/1977 | Dehnert | |
| 4,183,354 | 1/1980 | Sibley et al. | 128/711 |
| 4,350,164 | 9/1982 | Allain, Jr. | 128/639 |

FOREIGN PATENT DOCUMENTS

| | | | |
|---|---|---|---|
| 2513445 | 10/1975 | Fed. Rep. of Germany . | |
| 2839331 | 4/1980 | Fed. Rep. of Germany | 128/710 |
| 634218 | 1/1983 | Switzerland | 128/639 |

OTHER PUBLICATIONS

Vysotskaya et al, "An Electrode for Recording Biological Potentials", *Bio Med. Eng. (USA),* vol. 13, No. 4, Jul.–Aug. 1979, published Mar. 1980.
American Heart J., Oct. 1981, p. 757.
Biomedizinische Technik 25 (1980) No. 3, p. 70.
Cardiac Datacorp advertisement.
Derwent G1792A/32 [German Patent Specification No. 2,704,256 (1978)].
Jap. Electronic Engn. 63 (1972), p. 49f.
Minigraph advertisement.
Proc. 23rd Annual Conf. Engn. Med. Biol. 12 (1970), p. 249.

*Primary Examiner*—William E. Kamm
*Assistant Examiner*—Mitchell J. Shein
*Attorney, Agent, or Firm*—Jon S. Saxe; Bernard S. Leon; George W. Johnston

[57] ABSTRACT

A personal electrocardiology recorder having body electrodes for detecting heart action signals, an amplifier, a signal converter for converting the detected signals into signals recordable on magnetic tape, and a tape recorder, wherein the body electrodes are disposed directly on the tape recorder casing, the measuring and reference electrodes being disposed on a first wall and the earthing electrode being disposed on a wall other than the first wall, and wherein a microphone for recording a spoken description of the symptoms is provided. The recorder can be carried permanently by patients and can be switched on during the occurrence of corresponding symptoms for recording a diagnostically relevant ECG phase.

17 Claims, 10 Drawing Figures

PERSONAL ELECTROCARDIOLOGY RECORDER

BACKGROUND OF THE INVENTION

1. Field of the Invention

The invention concerns a personal electrocardiology recorder for detecting heart action signals.

2. Description

Electrocardiology tape recorders are used to detect and record or store heart action signals, more particularly in the supervision of patients and for stress tests in occupational and athletics medicine. The systems used differ fundamentally from one another in some respects, depending on their intended use and the aim of the supervision.

Tape recorders which are worn by a patient or subject and which are connected to the patient's skin by conventional body electrodes are known. Depending upon the kind of supervision required, recorders of this kind can record heart action signals for a specific time, as a rule 24 hours, on magnetic tape. Recorders of this kind are named after the pioneer in this area, Dr. N. Holter. In order to reduce the complexity of evaluating recordings, systems of this kind have been developed so that the recorder becomes actuated only in response to particular phenomena such as cardiac arrhythmia or the recorder switches itself on automatically at preselected time intervals. This enables the duration of use to be increased to up to 72 hours. It is usually impossible to extend this time any further since at that time the electrode contact on the patient's skin must be renewed by skilled personnel.

The evaluation of the taped electrocardiographs is usually carried out by the physician using a special evaluator in which the taped recording is displayed optically on a viewing screen and/or is transferred to paper.

Another system widely used in the United States of America is telephone ECG or EKG supervision. In response to the onset of a symptom such as cardiac arrhythmia, the patient gets into direct phone communication with a recorder in his physician's premises in order to phone in his heart action signals being monitored by a portable ECG amplifier. In a further development of this system, the ECG amplifier has a short-term storage capability which serves for the temporary storage of the signals, so that there ceases to be any need for a telephone to be immediately available. Facilities of this kind are of use only where there is a corresponding telephone transmitting, receiving and recording system. At present this is limited to the United States of America. Furthermore, transmission by telephone greatly restricts the accuracy of the recorded ECG.

Consequently, a simplified narrow-band ECG amplifier having more particularly a simplified electrode arrangement can be used. Equipment has therefore been proposed in which the electrodes are disposed directly on the ECG amplifier casing. Possible disturbances by the electrodes being spaced close-together are insignificant in view of the low quality of the transmission system.

SUMMARY OF THE INVENTION

The present invention provides a portable ECG recorder which a patient or subject can use for a prolonged period of time and which can be used for recording heart signals as required without special preparation during particular symptom phases.

In accordance with the invention, in a recorder of the aforementioned kind the electrodes are disposed directly on the tape recorder casing.

More particularly, the present invention concerns a hand-held electrocardiology recorder for recording heart signals. The recorder comprises a hand-held tape recording means having a casing with body electrodes disposed directly on the casing for detecting heart action signals. The recorder also includes amplifier means located within the casing for amplifying the signals detected by the body electrodes, and converter means located within the casing for converting the detected and amplified signals into recordable signals.

According to a particular embodiment of the recorder, the body electrodes comprise measuring, reference and grounding electrodes. The measuring and reference electrodes are disposed in spaced-apart relationship on a first wall of the recorder casing. Preferably, the grounding electrode is disposed on a wall of the recorder other than its first wall.

According to another embodiment of the recorder, one of the electrodes is integrated with a pressure switch.

According to another embodiment of the recorder, a microphone for recording acoustic signals, for example a short oral discription of the symptoms by the patient, is also provided.

BRIEF DESCRIPTION OF THE DRAWINGS

A preferred embodiment of the recorder in accordance with the invention will be described hereinafter with reference to the accompanying drawings in which.

DETAILED DESCRIPTION OF THE PREFERRED EMBODIMENT

The present invention concerns a hand-held electrocardiology recorder for recording heart signals. The recorder includes a hand-held tape recording means having a casing with body electrodes disposed directly on the casing for detecting heart action signals. Amplifier means are located within the casing for amplifying the signals detected by the body electrodes and converter means are located within the casing for converting the detected and amplified signals into recordable signals.

Figures 1A, 1B:
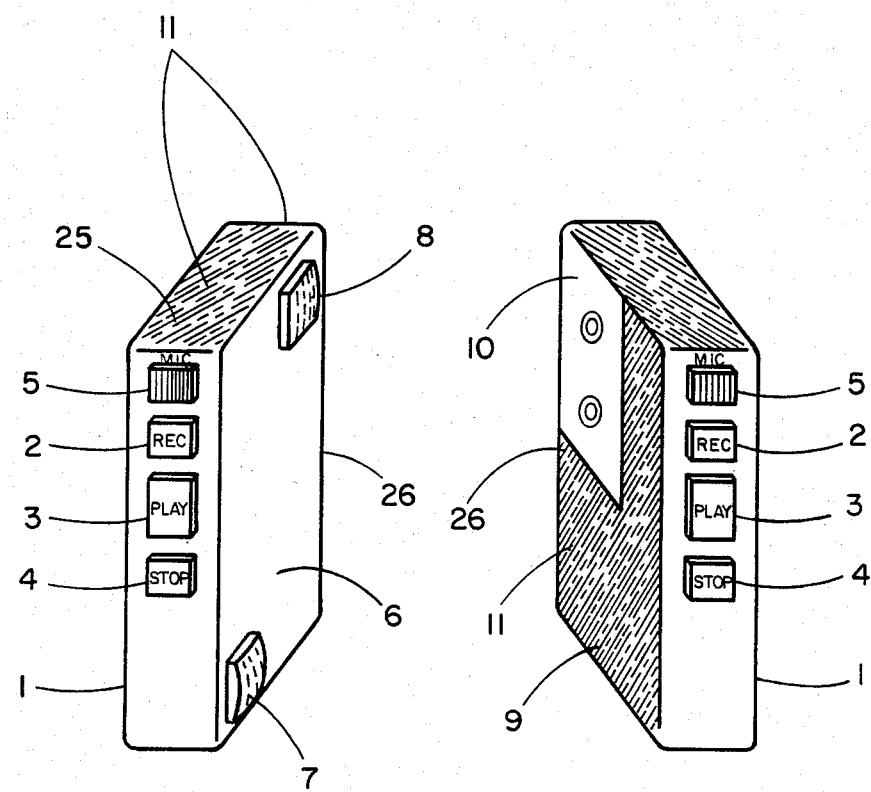
FIG. 1A is a perspective view of a recorder of the invention.
FIG. 1B is a second perspective view of the recorder.

FIGS. 1A and 1B illustrate prospective views of a recorder 1 of the invention. The recorder is a modified cassette tape recorder of the kind commercially available as hand-held dictating machines. On its longitudinal side of the casing of the recorder there can be seen recording, playback and stop buttons 2, 3 and 4, respectively. The buttons can, of course, be arranged and combined differently; for example, the stop button 4 can be omitted. A microphone 5 is disposed above the buttons. The user can record on the tape by means of the microphone 5 and, in connection with the intended use in the present connection, can set down, for example, a description of his symptoms after completion of the ECG recording.

Disposed on one flat side surface 6 of the recorder are two body electrodes 7, 8, these being preferably arranged at two diagonally opposite corners of the surface 6. These two electrodes are the actual measuring electrode 7 and a reference electrode 8. The reason for having a diagonal arrangement is to have maximum separation between the electrodes so as to achieve a differential basis for the ECG recording which is as large as possible.

Disposed on the opposite flat side 9 of the recorder is the cassette tape deck 10, which is identical to the cassette deck of commercially available dictating machines.

The recorder shown in FIG. 1 has in addition to the two electrodes 7, 8 a third electrode 11 in the form of an electrically conductive coating on sides 9, 25 and 26 of the casing. This third electrode serves as a grounding electrode. Any conventional conductive coating can be utilized as the grounding electrode. Suitable conductive coatings includes metal such as silver/silverchloride.

Figure 2:
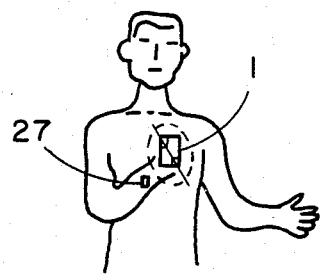
FIG. 2 is a diagrammatic view of the manner in which the patient holds the recorder to detect heart action signals.

Contact between the patient and this grounding electrode 11 is made by the patient holding the recorder in his right hand while pressing the flat side 6 with the electrodes 7, 8 as well as his right wrist 27 onto his chest in the manner shown in FIG. 2. A relatively considerable distance therefore exists between, on the one hand, the measuring electrode 7 and reference electrode 8 and, on the other hand, the grounding electrode 11 and wrist ground 27. Consequently, although all three electrodes are arranged on the casing, the distance between the grounding point 27 and the two measuring points is practically as great as is found in conventional ECG recording (diagnostic band width 0.05–100 Hz).

Figure 3:
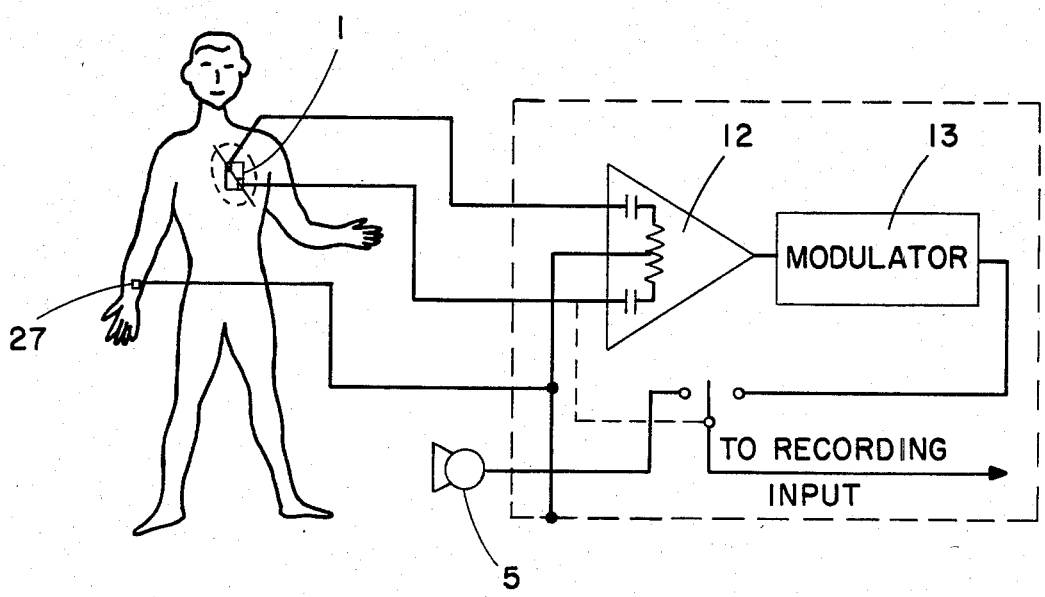
FIG. 3 is a schematic of the ECG part of the recorder.

Another feature, shown in FIG. 3, is that the recorder has a conventional ECG amplifier 12 with modulator 13, to which the two electrodes 7, 8 and the grounding electrode 11 are connected and whose output signals can be supplied to the recording head of the tape recorder.

For operation, the patient or subject places the recorder flat in his hand so that the buttons can be operated with the fingers and simultaneously places the surface of his hand or the ball of the thumb on the grounding electrode 11. Th recorder and patient's wrist are then pressed onto the lefthand side of the patient's chest as shown in FIG. 2 and the tape recorder started. After a short recording period, for example when the symptoms have disappeared, the patient or subject can dictate a description of his symptoms on to the tape via the microphone 5. Thereafter, the recorder can be put away until it is required for a subsequent recording.

Figure 4:
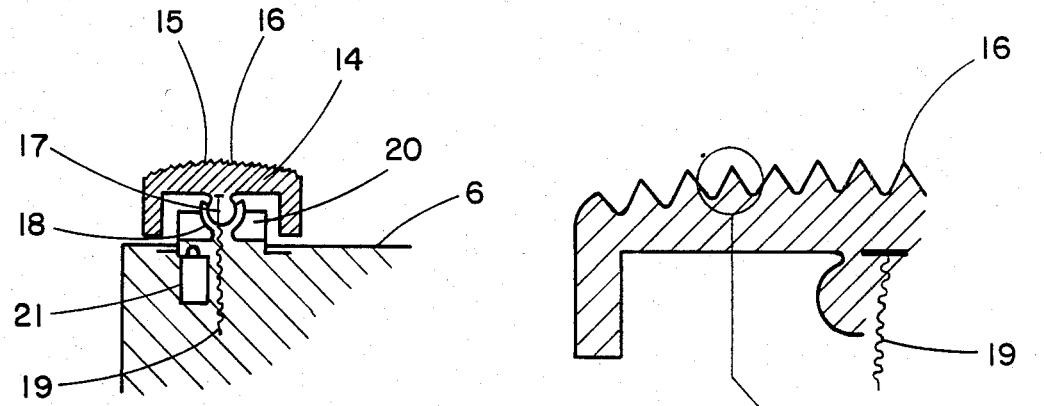
FIG. 4 is an enlarged, cross-sectional view of a portion of the recorder showing a measuring electrode having an integrated switch.
Figure 5A:
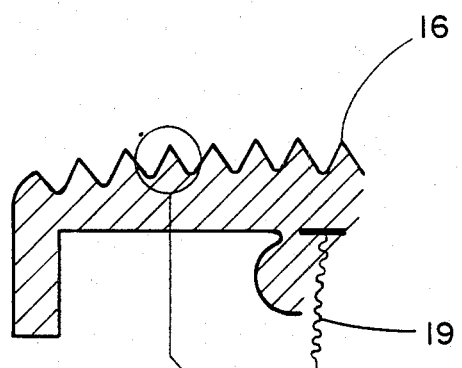
FIG. 5A is an enlarged view of the electrode surface of FIG. 4.
Figure 5B:
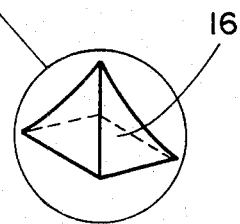
FIG. 5B is a further enlargement in perspective of the electrode surface of FIG. 5A.

FIGS. 4, 5A and 5B show a preferred embodiment of the measuring electrode 7. A cup or lid-shaped measuring head 14 has an arcuate top surface 15 adapted to be placed on the patient's skin. For improved contact with the skin, the surface of head 14 has a plurality of prismatic points or projections 16 which are shown in an enlarged perspective scale in Fig. 5B. Preferably the points are spaced about 1 mm apart. The surfaces of the points are coated with a conventional conductive metal or metal compound such as silver/silver chloride to prevent a polarization potential.

A projection 17 having a spherical head is disposed at the center of the inner underside of the measuring head 14. This male spherical head co-operates with a corresponding female hollow spherical socket 18 secured to the recorder casing to form a ball joint allowing the electrode to rotate about the ball joint socket 18 for adaptation to the curvature of the patient's body surface. A preferably spiral connecting line 19 extends from the projection 17 to the input of the ECG amplifier of FIG. 3.

The ball joint socket 18 can either be secured statically to the casing or, as in the present and preferred embodiment, can be disposed on a wall part 20 which is movably secured to the surface 6 to slide perpendicularly therefrom. Disposed on the inside of wall part 20 is a pressure switch 21 which is actuated when the wall part 20 is pressed into the casing by contact of measuring head 14 with the skin. Switch 21 (see also FIG. 3) is connected between the output of the ECG amplifier 12 and the tape recorder recording head so that the ECG signals are recorded when, due to the recorder being pressed against the partient's body, the electrode 7 and the wall part 20 actuate the switch 21. Consequently, a predetermined minimum pressure acts on the electrode 7 to initiate recording and thus satisfactory contact for the ECG recording is provided. In the absence of pressure on the electrode (i.e. when the switch 21 is not being actuated) the user can dictate on to the tape via the microphone.

Figure 6:
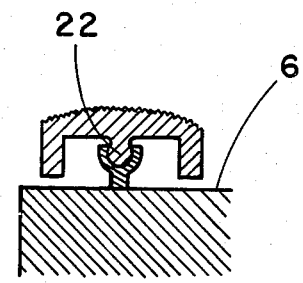
FIG. 6 is an enlarged, cross-sectional view of another portion of the recorder showing a reference electrode.

Since reference electrode 8 does not need a pressure switch, the electrode is of simpler construction than the electrode 7, as shown in FIG. 6. Preferably, it is similarly connected by a ball joint configuration 22 to the casing but the female element of the ball joint is in this case rigidly secured to the casing on side 6. Apart from the extra feature for operating the pressure switch, the electrodes 8 and 7 are of identical components and construction.

Figure 7:
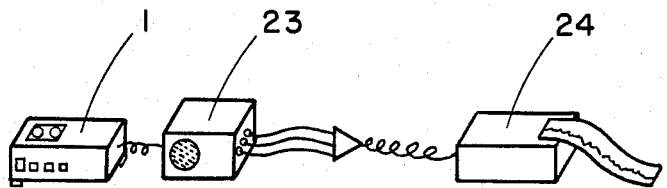
FIG. 7 is a diagrammatic view of the equipment for transcribing signals recorded on the recorder.

For it to be possible to evaluate the taped ECG signal, the same is converted into an optical signal. Also, the spoken information on the tape is listened to. An arrangement of the kind shown in FIG. 7 can be used for this purpose. The recorder 1 is directly connected to a playback device 23 which comprises a demodulator and a loudspeaker and which enables the speech on the tape to be heard. The demodulator output is connected to a commercially available electrocardiograph 24 which transcribes the ECG signal in the usual manner.

Instead of the recorder 1 being directly connected to the playback device 23, a special playback facility can, of course, be used. This is advisable, for example, when the recorded cassette is sent to the treating physician for evaluation.

Figure 8:
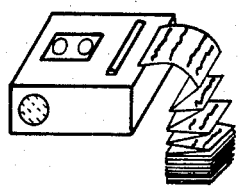
FIG. 8 shows an alternative to the equipment shown in FIG. 7.

Another possible way of transcribing the ECG's is shown in FIG. 8. The transcriber diagrammatically shown here is a high-speed recorder having so-called thermopaper which is a compact means of making the transcription. This device also has a loudspeaker for listening to tape-recorded comments.

The recorder described hereinbefore has the great advantage that the patient can wear it for a prolonged time, for example several months, without using it until an event worthwhile recording occurs. This has been impossible with the conventional so-called Holter recorders since the contact of the conventional ECG electrodes with the skin must be renewed after at most 72 hours by skilled personnel. Also, it would be too much to expect the patient to wear ECG electrodes for a long time when it is completely impossible to determine when a significant recording is possible.

Convenience of this degree has previously been associated exclusively with the phone-in recorders, which have the disadvantage of being usable only in very specific conditions and of providing a comparatively poor quality recording. However, the recorder in accordance with the invention satisfies a long felt need for a complete hand-held, long-term ECG diagnosis tool which provides the physician with all the information he needs to assess the ECGs. To this extent, therefore, the recorder in accordance with the invention is superior to the phone-in facilties.

While the invention has been described in conjunction with certain embodiments, it is understood that various modifications and changes may be made without departing from the spirit and scope of the invention.

For example, the pressure switch 21 could be incorporated into reference electrode 8 instead of measuring electrode 7. The grounding electrode need be coated on one of the surfaces 9, 25 or 26. The grounding electrode could be a separate element instead of a coating.

According to a further embodiment (not shown) of the invention the tape recorder is separate from the ECG amplifier portion, whereby the recorder is insertable into a case containing the ECG amplifier like a module. This case is provided with the electrodes and the necessary switches. The commercially available device Sony M-100 is suitable for this embodiment. This device has a loudspeaker which in particularly urgent cases can be used for transmission of the record via telephone.

I claim:

1. A hand-held electrocardiology recorder for recording heart signals of a patient comprising:
   (a) a hand-held tape recording means having a casing with at least first and second walls;
   (b) a measuring electrode and a reference electrode disposed on the first wall of the casing for contacting the chest of the patient and detecting heart signals;
   (c) a grounding electrode disposed on the second wall of the casing such that electrical contact between the patient's chest and the grounding electrode can be made by the patient's hand touching the grounding electrode while the patient's wrist contacts the chest;
   (d) amplifier means located within the casing for amplifying the signals detected by the electrodes; and
   (e) converter means located within the casing for converting the detected and amplified signals into recordable signals.

2. The recorder of clam 1 wherein the amplifier means is an amplifier.

3. The recorder of claim 2 wherein the converter means is a signal converter.

4. The recorder of claim 3 wherein the measuring and reference electrodes are disposed in spaced-apart relationship on the first wall.

5. The recorder of claim 4 wherein the grounding electrode is a conductive coating.

6. The recorder of claim 4 wherein the measuring electrode includes:
   (a) an electrode measuring head; and
   (b) ball joint means for mounting the electrode measuring head to the first wall and permitting pivoting of the electrode measuring head thereon.

7. The recorder of claim 6 wherein the electrode measuring head has an arcurate configured surface portion with a plurality of contact projections extending outwardly.

8. The recorder of claim 7 wherein the projections are coated with a conductive metal.

9. The recorder of claim 4 wherein the reference electrode includes:
   (a) an electrode reference head; and
   (b) ball joint means for mounting the electrode measuring head to the first wall portion and permitting pivoting of the electrode reference head thereon.

10. The recorder of claim 9 wherein the electrode reference head has an arcuate-configured surface portion with a plurality of contact projections extending outwardly.

11. The recorder of claim 10 wherein the projections are coated with a conductive metal.

12. The recorder of claim 3 wherein the reference and measuring electrodes are disposed in diagonally opposing portions of said first wall.

13. The recorder of claim 1 wherein at least one of the body electrodes includes pressure switch means for selectively actuating the tape recording means.

14. The recorder of claim 1 wherein the tap recording means includes a microphone for receiving acoustic signals.

15. A hand-held, self-contained electrocardiology recorder for recording heart signals on magnetic tape comprising:
   (a) a hand-held tape recording means having a casing with a first wall;
   (b) a measuring electrode;
   (c) a reference electrode, said measuring and reference electrodes located and disposed in spaced-apart relationship on said first wall of the casing for detecting heart signals;
   (d) grounding electrode located and disposed on the casing on other than the first wall thereof;
   (e) amplifier located within the casing for amplifying the signals detected by the measuring and reference electrodes; and
   (f) converter means located within the casing for converting the detected and amplified signals into signals recordable on magnetic tape.

16. The recorder of claim 15 wherein the measuring electrode includes:
   (a) an electrode measuring head having an arcuate-configured surface portion with a plurality of electrically conductive projections extending outwardly from the surface portion; and
   (b) ball joint means for mounting the electrode measuring head to the first wall of the casing and permitting pivoting of the electrode measuring head thereon.

17. The recorder of claim 16 wherein at least one of the electrodes includes a pressure switch for actuating the tape recording means.

* * * * *